US00PP35735P2

(12) United States Plant Patent
Berry

(10) Patent No.: US PP35,735 P2
(45) Date of Patent: Apr. 9, 2024

(54) ***HIBISCUS* PLANT NAMED 'JBG AH-59'**

(50) Latin Name: *Hibiscus rosa-sinensis*
Varietal Denomination: JBG AH-59

(71) Applicant: Capstone Plants, Inc., Grand Saline, TX (US)

(72) Inventor: James Berry, Emory, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 18/073,741

(22) Filed: Dec. 2, 2022

(51) Int. Cl.
*A01H 5/00* (2018.01)
*A01H 6/60* (2018.01)

(52) U.S. Cl.
USPC ..... Plt./257

(58) Field of Classification Search
USPC ..... Plt./226, 257
See application file for complete search history.

*Primary Examiner* — Karen M Redden
(74) *Attorney, Agent, or Firm* — The Webb Law Firm

(57) ABSTRACT

A new and distinct *Hibiscus* plant having pink colored flowers and a compact growth habit.

2 Drawing Sheets

Botanical classification: *Hibiscus rosa-sinensis.*
Varietal denomination: 'JBG AH-59'.

BACKGROUND OF THE INVENTION

The present invention comprises a new and distinct *Hibiscus* plant having the varietal name 'JBG AH-59'. The new variety is the result of a planned breeding program with the purposes of developing *Hibiscus rosa-sinensis* plants that exhibit whitefly and leaf spot resistance, propagation and production efficiencies, durable and exotic flowers, and abundant flowering. 'JBG AH-59' is the result of a cross conducted in Grand Saline, Texas between *Hibiscus rosa-sinensis* varieties 'RH-07' (female parent, unpatented) and 'JBN 12002' (male parent, U.S. Plant Pat. No. 27,304). The new variety was selected in February of 2016 in Grand Saline, Texas and the first asexual reproduction of the new variety was conducted by semi-hardwood cuttings in June of 2016 in Grand Saline, Texas. 'JBG AH-59' has been trial and field tested and has been found to retain its distinctive characteristics and remain true to type through successive propagations. The present invention has not been evaluated under all possible environmental conditions. However, it has been found to thrive in production and adapt well to the environment in Homestead, Florida. The phenotype may vary with variations in environment without a change in the genotype of the plant.

'JBG AH-59' is similar to its female parent in pink flower color, upright growth habit, abundant flower production, and exhibiting high whitefly resistance. 'JBG AH-59' differs from its female parent in having smaller flower petals that are less ruffled and have less overlap. Further, 'JBG AH-59' exhibits a smaller overall flower size than its female parent, but has a more upright growth habit and increased vigor. 'JBG AH-59' is similar to its male parent in leaf shape and color, having thin flower petals, and lacking a flower eye. However, 'JBG AH-59' differs from its male parent in being more compact and less upright in habit, with better branching. Further, 'JBG AH-59' differs from its male parent in flower color.

When 'JBG AH-59' is compared to *Hibiscus rosa-sinensis* variety having a commercial name of "Trophy Wife" (unpatented), both varieties have a pink flower color, similar male parent, and strong heat tolerance. However, 'JBG AH-59' has smaller flowers with thinner petals, lacks a flower eye, and less petal ruffling than "Trophy Wife".

The following traits distinguish 'JBG AH-59' as a new and distinct cultivar from other *Hibiscus* varieties known to the breeder:

1. Profuse flowering even at high temperatures;
2. Well-mounded and compact habit;
3. Rounded foliage with crenate margins; and
4. Desirable pollen production.

DESCRIPTION OF THE DRAWINGS

The accompanying photographic images illustrate the new variety at approximately eight months of age, with the colors being as nearly true as is possible with color illustrations of this type.

DESCRIPTION OF THE PLANT

Figure 1:
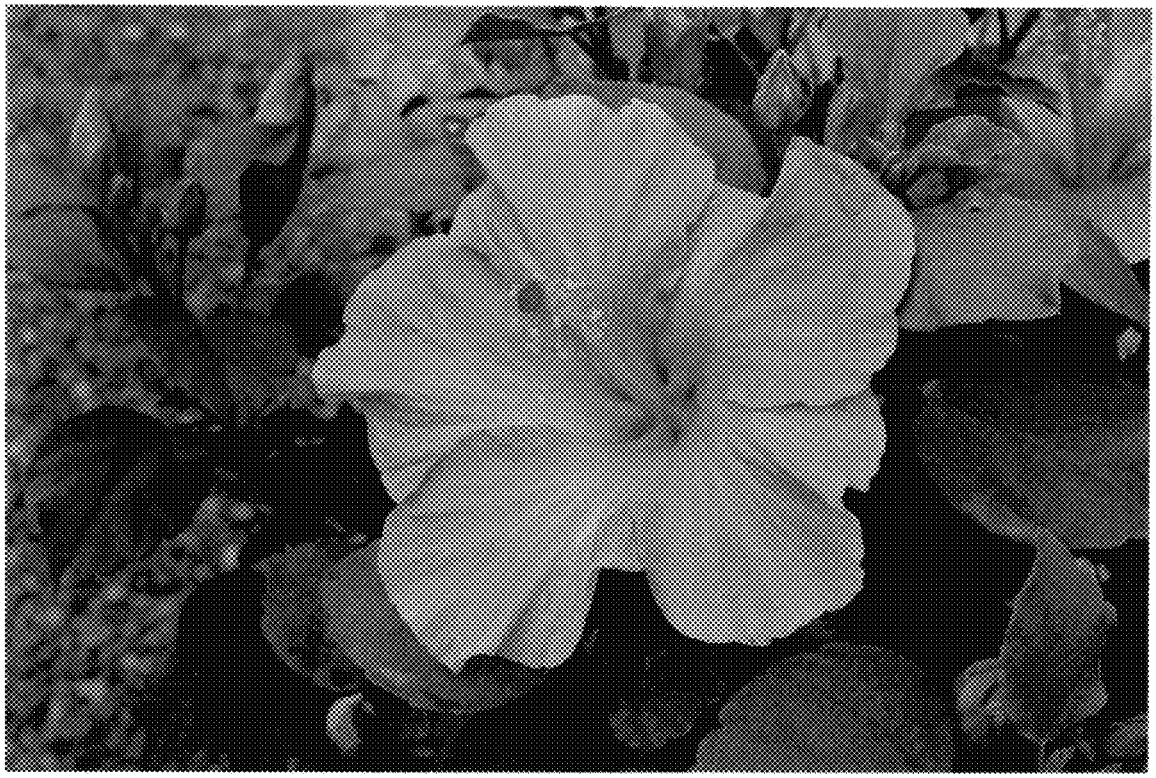
FIG. 1 illustrates a close-up view of a flower of the new variety.
Figure 2:
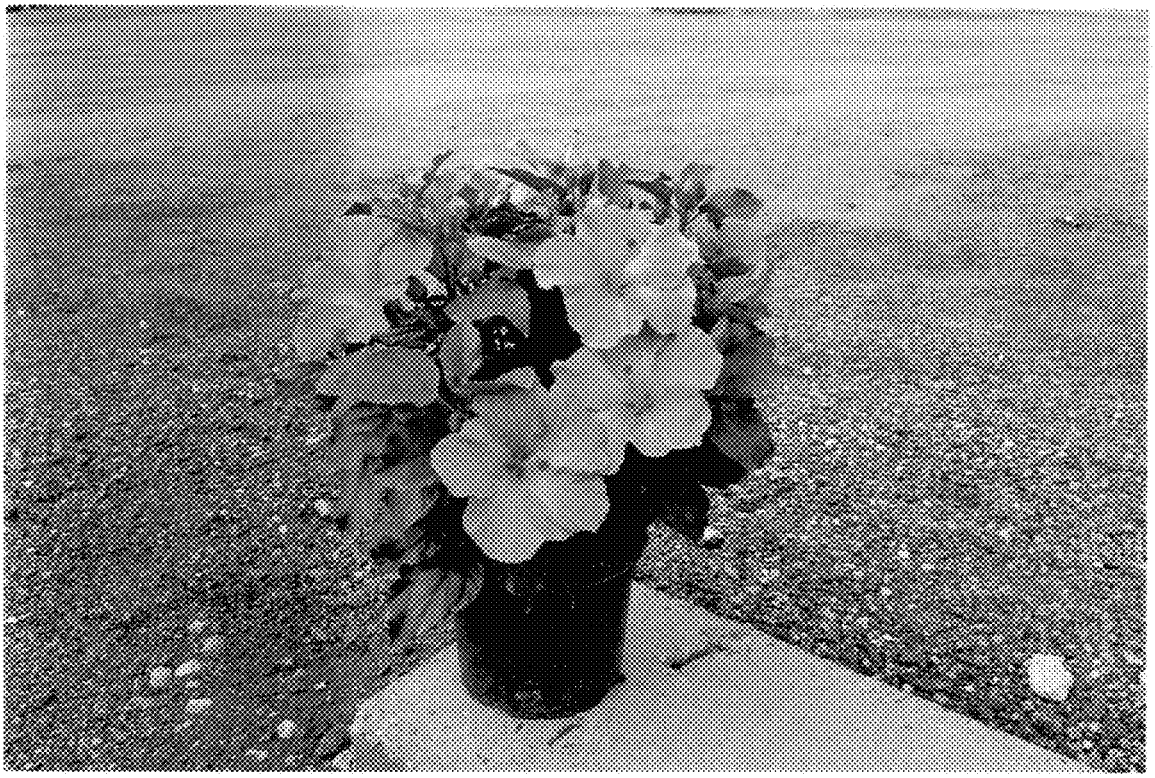
FIG. 2 illustrates an entire plant of the new variety.

The following detailed description sets forth the characteristics of the new variety. The plants were grown in 23 cm containers in a greenhouse with a minimum temperature of approximately 13° C. and about 30% light shade in the summer months. The color readings and measurements were taken indoors under fluorescent lights with natural light from a window nearby on approximately eight month old plants. Color references are primarily to The 1995 R.H.S. Colour Chart of The Royal Horticultural Society of London, 3$^{rd}$ Edition, except where general color terms are used.

PLANT

Time to initiate roots: About 12 days at an average of 24° C.
Time to develop roots: About 50 days at an average of 21-24° C.

Time to produce a finished flowering plant from a rooted cutting: About 12-16 weeks in a 1 gallon/20.0 cm diameter container.

Specific disease/pest resistance: Resistance to whitefly (*Trialeurodes vaporariorum*) and bacterial leaf spot (*Pseudomonas* spp.).

Heat/cold tolerance: Thrives above 13° C., but expires at temperatures of 0° C. and below.

Drought tolerance: Moderate to none.

Plant:

*Type*.—Tropical, ornamental shrub.

*Habit*.—Upright; well-mounded.

*Height*.—40.6 cm from the top of the pot to the top of the plant.

*Spread*.—55.9 cm.

*Vigor*.—Moderate.

*Rooting*.—Coarse and well-branched.

Stem:

*Number per plant*.—7.

*Length*.—35.6-38.1 cm.

*Width*.—5.0 mm on immature stems; 20.0 mm on mature stems.

*Texture*.—Immature: Slightly textured with tan bumps present. Mature: Very coarse with dark brown bumps present.

*Strength*.—Firm.

*Branch arrangement*.—Alternate.

*Branch number*.—21.

*Internode length*.—24.0-33.0 mm.

*Color*.—Immature: 144A. Mature: 199B.

*Stipules*.—Number per node: 2. Shape: Spinose. Length: 7.0 mm. Width: 1.0 mm. Surface texture: Smooth. Apex: Acute. Base: Linear. Margin: Entire. Color: 143A.

Foliage:

*Arrangement*.—Alternate.

*Size of leaf*.—Length: 7.9 cm. Width: 7.0 cm.

*Shape of leaf* (*generally*).—Ovate.

*Shape of apex*.—Acute.

*Shape of base*.—Cordate.

*Texture*.—Upper surface: Smooth with a slight texture from venation. Lower surface: Relatively smooth with a heavier vein texture.

*Margin type*.—Crenate.

*Color*.—Young leaves: Upper surface: 141A. Lower surface: 137C. Mature leaves: Upper surface: 189A. Lower surface: 137D.

*Veins*.—Venation type: Palmate. Color: Upper surface: 137A. Lower surface: 146B.

*Petiole*.—Length: 3.2 cm. Diameter: 4.0 mm. Texture: Slightly textured. Color: 143B.

FLOWERS

Buds (described when closed):

*Shape*.—Ovate.

*Diameter*.—1.9 cm.

*Length*.—4.4 cm.

*Color*.—47D.

Natural flowering season: Year round in Grand Saline, Texas.

Flower type and habit: Single with slightly overlapping petals.

Fragrance: None.

Flowers:

*Number per stem*.—1-2.

*Overall depth*.—2.0 cm.

*Overall diameter*.—14.0 cm.

*Shape*.—Rotate.

*Lastingness*.—2 days on the plant.

*Petals*.—Number: 5. Arrangement: Simple. Length: 9.0 cm. Width: 6.7 cm. Shape: Ovate. Apex: Obtuse. Base: Acute. Margin: Entire. Texture/appearance: Upper surface: Smooth. Lower surface: Smooth and velvety with heavy venation texture. Color: When opening: Upper surface: 53D. Lower surface: 181C. Fully opened: Upper surface: 51B. Lower surface: 181D.

*Calyx*.—Form: Fused. Overall length: 2.5 cm. Overall diameter: 1.9 cm. Sepals/calyx lobes: Number: 5. Shape: Lanceolate. Apex: Acute. Margin: Entire. Texture: Smooth with slightly textured edges. Color: Outer surface: 143A. Inner surface: 146D.

*Epicalyx*.—Length: 2.2 cm. Width: 3.0 mm. Texture: Slightly textured. Color: 143A. Sepal-like bracts: Not present.

*Bracts*.—Not present.

*Peduncle*.—Length: 10.0 mm. Diameter: 3.0 mm. Strength: Firm. Angle: 20°. Texture: Slightly coarse. Color: 144A.

Reproductive organs:

*Gynoecium*.—Pistils: Number: 1. Length: 7.9 cm. Stigma: Number: 5. Shape: Round. Length: 2.0 mm. Diameter: 2.0 mm. Color: 187A. Style: Length: 7.1 cm. Width: 5.0 mm. Color: 182B. Ovary: Shape: Ovate. Length: 12.0 mm. Width: 7.0 mm. Color: 199D.

*Androecium*.—Stamens: Number: 78. Position: Below the stigma on the style. Anther: Shape: U-shaped. Diameter: 1.0 mm. Color: 21A. Filament: Length: 6.0 mm. Width: 1.0 mm. Color: 52B. Pollen: Color: 23A. Amount (generally): Moderate to high.

SEEDS

Seeds: None produced.

I claim:

1. A new and distinct variety of *Hibiscus* plant named 'JBG AH-59', substantially as illustrated and described herein.